US012779017B2

(12) United States Patent
Zhou et al.

(10) Patent No.: US 12,779,017 B2
(45) Date of Patent: Nov. 3, 2026

(54) EXENATIDE ANALOG

(71) Applicant: CHENGDU AODA BIOTECHNOLOGY CO., LTD, Chengdu (CN)

(72) Inventors: Shuliang Zhou, Chengdu (CN); Peng Wang, Chengdu (CN); Lan Deng, Chengdu (CN)

(73) Assignee: CHENGDU AODA BIOTECHNOLOGY CO., LTD, Chengdu (CN)

( * ) Notice: Subject to any disclaimer, the term of this patent is extended or adjusted under 35 U.S.C. 154(b) by 385 days.

(21) Appl. No.: 17/764,041

(22) PCT Filed: Sep. 15, 2020

(86) PCT No.: PCT/CN2020/115222

§ 371 (c)(1),
(2) Date: Mar. 25, 2022

(87) PCT Pub. No.: WO2021/057541

PCT Pub. Date: Apr. 1, 2021

(65) Prior Publication Data

US 2022/0347270 A1 Nov. 3, 2022

(30) Foreign Application Priority Data

Sep. 25, 2019 (CN) ......................... 201910908468.3

(51) Int. Cl.
*A61K 38/26* (2006.01)
*A61P 3/10* (2006.01)

(52) U.S. Cl.
CPC ................ *A61K 38/26* (2013.01); *A61P 3/10* (2018.01)

(58) Field of Classification Search
None
See application file for complete search history.

(56) References Cited

U.S. PATENT DOCUMENTS

2006/0178304 A1 8/2006 Juul-Mortensen et al.
2012/0196798 A1 8/2012 Wang et al.
2019/0119347 A1 4/2019 Kim et al.

FOREIGN PATENT DOCUMENTS

CN 102827270 A 12/2012
CN 105985425 A 10/2016
CN 106554404 A 4/2017
CN 109641035 A 4/2019
CN 110551203 A 12/2019
JP 2006514035 A 4/2006
JP 2008500262 A 1/2008
WO 2004056313 A2 7/2004
WO 2017178829 A1 10/2017

OTHER PUBLICATIONS

Yap et al. Exendin-4 from Heloderma suspectum venom: From discovery to its latest application as type II diabetes combatant, Basic Clin Pharmacol Toxicol. 2019; 124:513-527 (Year: 2019).*
Coskun et al. LY3298176, a novel dual GIP and GLP-1 receptor agonist for the treatment of type 2 diabetes mellitus: From discovery to clinical proof of concept, Molecular Metabolism 18 (2018) 3-14 (Year: 2018).*
Wang et al. "Synthesis of Dehydroamino Acids and Their Applications in the Drug Research and Development," Progress in Chemistry, 2020, 32(1): 55-71 (Year: 2020).*
Siodlak. α,β-Dehydroamino acids in naturally occurring peptides, Amino Acids (2015) 47:1-17 (Year: 2015).*
English translation of CN106554404A obtained from Google translate on Jul. 10, 2025 (Year: 2025).*
Donnelly D. The structure and function of the glucagon-like peptide-1 receptor and its ligands. Br J Pharmacol. May 2012; 166(1):27-41 (Year: 2012).*
Search Report dated Dec. 7, 2023 for European patent application No. 20869930.6.
Simonsen L et al., "Exendin-4, but not glucagon-like peptide-1, is cleared exclusively by glomerular filtration in anaesthetised pigs", Diabetologia (2006) 49: 706-712.
International Search Report for PCT/CN2020/115222 mailed Dec. 2, 2020, ISA/CN.
Susan L. Samson et al., A Plethora of GLP-1 Agonists: Decisions About What to Use and When, Current Diabetes Reports, vol. 16, Oct. 20, 2016, article 120, pp. 1-13.
Fan Yi et al., GLP-1 biology and GLP-1 based antidiabetic therapy, Journal of Chinese Pharmaceutical Sciences, vol. 22, Dec. 31, 2013, pp. 7-27.
First Office Action dated Jun. 26, 2023 for Japanese patent application No. 2022-519514, English translation provided by Global Dossier.

* cited by examiner

*Primary Examiner* — Christina Bradley
(74) *Attorney, Agent, or Firm* — Yue (Robert) Xu; Apex Attorneys at Law, LLP

(57) ABSTRACT

The present invention relates to the field of pharmaceutical synthesis, and disclosed is an exenatide analog. The exenatide analog is used for preparing a pharmaceutical composition for treating diseases. Also disclosed is a use of the pharmaceutical composition in preparation of medicines for treating at least one of the following diseases: type-II diabetes, impaired glucose tolerance, type-I diabetes, obesity, hypertension, metabolic syndrome, dyslipidemia, cognitive disorder, atherosclerosis, myocardial infarction, coronary heart disease, cardiovascular diseases, stroke, inflammatory bowel syndrome and/or dyspepsia or gastric ulcer, hepatic fibrosis diseases, and pulmonary fibrosis diseases.

8 Claims, No Drawings

Specification includes a Sequence Listing.

EXENATIDE ANALOG

CROSS REFERENCE TO RELATED APPLICATIONS

This application is a U.S. National Phase application based upon PCT Application No. PCT/CN2020/115222 filed on Sep. 15, 2020, which claims the priority of Chinese Patent Application No. 201910908468.3, filed with the China National Intellectual Property Administration on Sep. 25, 2019, and titled with "EXENATIDE ANALOG", which is hereby incorporated by reference in its entirety.

SEQUENCE LISTING

This application contains references to amino acid sequences and/or nucleic acid sequences which have been submitted concurrently herewith as the sequence listing text file entitled "220026-APXU-AODA_ST25_v2.txt", file size 6,259 bytes, created on Apr. 9, 2025. The aforementioned sequence listing is hereby incorporated by reference in its entirety pursuant to 37 CFR 1.835(b)(2).

FIELD

The present disclosure relates to an exenatide analog and use thereof, and the analog is a glucagon-like peptide-1 (GLP-1) analog.

BACKGROUND

Diabetes has become the third non-communicable disease after cardiovascular and cerebrovascular diseases and tumors. The World Health Organization (WHO) predicts that in 2030, there will be more than 360 million people in the world affected by diabetes, of which more than 90% are type II diabetes. GLP-1, a secretin secreted by intestinal L cells, has functions such as promoting insulin secretion, inhibiting glucagon release, stimulating the proliferation of islet B cells, inducing the regeneration of islet B cells, preventing the apoptosis of islet B cells, improving sensitivity to insulin and increasing utilization of glucose, which plays an important role in the occurrence and development of type II diabetes. In patients with type II diabetes, the "incretin effect" is impaired, which is mainly manifested in that the increase in the concentration of GLP-1 after meals is less than that of normal people, but the promotion on insulin secretion and hypoglycemic effects are not significantly impaired. Therefore, GLP-1 can be used as an important target for the treatment of type II diabetes. Also, the function of GLP-1 is glucose concentration-dependent, and its hypoglycemic properties are the basis and guarantee for the clinical safety, thus eliminating the concern that the existing diabetes treatment drugs and schemes may cause severe hypoglycemia in patients. Therefore, GLP-1 has broad application prospects in the field of diabetes treatment.

However, the clinical application of GLP-1 also faces huge problems. The GLP-1 produced by the human body is very unstable and easily degraded by dipeptidyl peptidase IV (DPP-IV) in the body. GLP-1 has a short half-life in plasma, which limits its clinical application.

In addition, many patients with type II diabetes are reluctant to be administered by injection daily, so the development of safe and effective GLP-1 analogs that can be administered once a week has greater prospects.

SUMMARY

The present disclosure provides an exenatide analog and use thereof, and the analog is a glucagon-like peptide-1 (GLP-1) analog.

In order to achieve the above object, the present disclosure first provides a compound having structure I, a pharmaceutically acceptable salt thereof, a solvate thereof, a chelate thereof or non-covalent complex thereof, a prodrug thereof, or any mixture thereof.

AA1-GLu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-AA2(R)-AA3 (SEQ ID NO: 1)

Structure I

AA1 in structure I is:

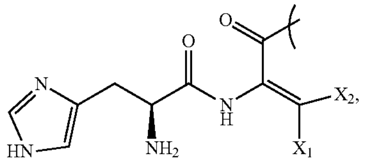

$X_1$ and $X_2$ are each independently selected from the group consisting of H, $CH_3$, $CH(CH_3)_2$, $C(CH_3)_3$, $CH(CH_2CH_3)_2$, $C(CH_2CH_3)_3$, $CH(CH_2CH_2CH_3)_2$, $C(CH_2CH_2CH_3)_3$, $CH(CH(CH_3))_2$, $C(CH(CH_3))_3$, $CH_2CH_3$, $CH_2CH(CH_3)_2$, $CH_2C(CH_3)_3$, $CH_2CH(CH_2CH_3)_2$, $CH_2C(CH_2CH_3)_3$, $CH_2CH(CH_2CH_2CH_3)_2$, $CH_2C(CH_2CH_2CH_3)_3$, $CH_2CH(CH(CH_3))_2$, and $CH_2C(CH(CH_3))_3$;

AA2 of structure I is selected from the group consisting of Lys, Dah, Orn, Dab and Dap;

AA3 of structure I is $NH_2$ or OH; and

R of structure I is $HO_2C(CH_2)_{n1}CO$—(γGlu)$_{n2}$-(PEG$_{n3}$(CH$_2$)$_{n4}$CO)$_{n5}$—, n1 is an integer from 10 to 20, n2 is an integer from 1 to 5, n3 is an integer from 1 to 30, n4 is an integer from 1 to 5, and n5 is an integer from 1 to 5.

The present disclosure also provides a pharmaceutical composition comprising the compound according to the present disclosure, as well as use of the pharmaceutical composition of the present disclosure in the manufacture of a medicament for treating a disease.

Preferably, the pharmaceutical composition is used in the manufacture of a medicament for treating a disease, wherein the disease is selected from the group consisting of type II diabetes, impaired glucose tolerance, type I diabetes, obesity, hypertension, metabolic syndrome, dyslipidemia, cognitive disorder, atherosclerosis, myocardial infarction, coronary heart disease, cardiovascular disease, stroke, inflammatory bowel syndrome, dyspepsia, gastric ulcer, liver fibrotic disease, pulmonary fibrotic disease and a combination thereof.

Preferably, the pharmaceutical composition is used in the manufacture of a medicament for treating type II diabetes with delayed efficacy and/or preventing the exacerbation of type II diabetes.

Preferably, the pharmaceutical composition is used in the manufacture of a medicament for reducing food intake, reducing β-cell apoptosis, increasing islet β-cell function, increasing β cells and/or restoring β-cell sensitivity to glucose.

The present disclosure further provides a method for regulating blood glucose in the body by administering the compound to a subject in need thereof.

More contents of the present disclosure are described in detail below, or some of them may be illustrated in the embodiments of the present disclosure.

Unless otherwise indicated, the amounts of various components and the reaction conditions used herein may be interpreted as "roughly" or "approximately" in any case. Correspondingly, unless otherwise specified, the numerical parameters quoted in the following and in the claims are approximate parameters, and different numerical parameters may be obtained due to differences in standard errors under respective experimental conditions.

When there is disagreement or doubt between the chemical structural formula and the chemical name of a compound herein, the chemical structural formula is used to exactly define the compound. The compound described herein may contain one or more chiral centers, and/or double bonds and the like, and may also exist as stereoisomers, including double bond isomers (such as geometric isomers), optically active enantiomers or diastereomers. Accordingly, any chemical structure within the scope of the description herein, whether part of or the whole structure containing similar structures above, includes all possible enantiomers and diastereomers of the compound, including any of the pure stereoisomers (such as pure geometric isomers, pure enantiomers or pure diastereomers) and any mixture of these isomers. These racemic and stereoisomeric mixtures can also be further resolved into their constituent enantiomers or stereoisomers by those skilled in the art using different separation techniques or chiral molecular synthesis methods.

The compounds having structure I include, but are not limited to, optical isomers, racemates and/or mixtures of these compounds. In the above case, pure enantiomer or diastereomer, such as optical isomer, can be obtained by asymmetric synthesis or resolution of racemates. Resolution of racemates can be accomplished by various methods, such as conventional recrystallization with a resolution-promoting agent, or by chromatography. In addition, compounds having structure I also include cis- and/or trans-isomers with double bonds.

The compound of the present disclosure includes, but is not limited to, compounds of structure I and all various pharmaceutically acceptable forms. The various pharmaceutically acceptable forms include various pharmaceutically acceptable salts, solvates, complexes, chelates, non-covalent complexes, prodrugs based on the aforementioned substances and any mixture of the aforementioned forms.

The compound having structure I provided by the present disclosure has stable properties, is not easily degraded by dipeptidyl peptidase IV (DPP-IV) in the body, is a long-acting GLP-I analog, and has a significant hypoglycemic effect.

DETAILED DESCRIPTION

The present disclosure discloses a glucagon-like peptide-1 (GLP-1) analog and use thereof, and those skilled in the art can learn from the content of the present disclosure and appropriately improve relevant parameters to achieve. It should be particularly pointed out that all similar substitutions and modifications are obvious to those skilled in the art, and they are deemed to be included in the present disclosure. The method of the present disclosure has been described through the preferred embodiments, and it is obvious that relevant persons can achieve and apply the techniques of the present disclosure by changes or appropriate modifications and combinations of the compound and the preparation method described herein, without departing from the content, spirit and scope of the preset disclosure.

The names corresponding to the abbreviations used in the present disclosure are shown in the following table:

| Abbreviation | Name | Abbreviation | Name |
|---|---|---|---|
| Fmoc | 9-Fluorenemethoxycarbonyl | OtBu | Tert-butoxy |
| tBu | Tert-butyl | Boc | Tert-butoxycarbonyl |
| Trt | Trityl | Pbf | (2,3-Dihydro-2,2,4,6,7-pentamethylbenzofuran-5-yl)sulfonyl |
| Ala | Alanine | Leu | Leucine |
| Arg | Arginine | Lys | Lysine |
| Asn | Asparagine | Met | Methionine |
| Asp | Aspartic acid | Phe | Phenylalanine |
| Cys | Cysteine | Pro | Proline |
| Gln | Glutamine | Ser | Serine |
| Glu | Glutamic acid | Thr | Threonine |
| Gly | Glycine | Trp | Tryptophan |
| His | Histidine | Tyr | Tyrosine |
| Ile | Isoleucine | Val | Valine |
| Dap | 2,3-Diaminopropionic acid | Dab | 2,4-Diaminobutyric acid |
| Orn | Ornithine | Dah | 2,7-Diaminoheptanoic acid |
| Dhser | Dehydroxyserine | Dhthr | Dehydroxythreonine |
| Dhval | 2,3-Didehydrovaline | | |

Example 1 Preparation of Compound 1

(SEQ ID NO: 2)

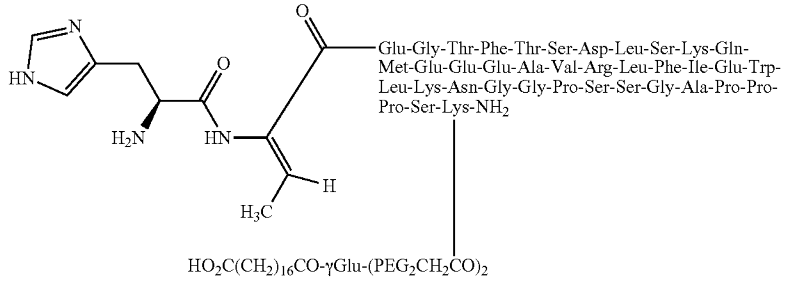

The preparation method comprises: preparing a peptide resin by a solid-phase polypeptide synthesis method, then subjecting the peptide resin to acidolysis to obtain a crude product, and finally purifying the crude product to obtain a pure product; wherein the step of preparing a peptide resin by a solid-phase polypeptide synthesis method is to sequentially couple the protected amino acid or fragment corresponding to the following sequences to a carrier resin by solid-phase coupling synthesis to prepare the peptide resin.

In the above preparation method, the amount of the Fmoc-protected amino acid or the protected amino acid fragment is 1.2-6 times, preferably 2.5-3.5 times of the total moles of the resin charged.

In the above preparation method, the degree of substitution of the carrier resin is 0.2-1.0 mmol/g of resin, preferably 0.3-0.5 mmol/g of resin.

As a preferred embodiment of the present disclosure, the solid-phase coupling synthesis method comprises: removing the Fmoc protecting group from the protected amino acid-resin obtained in the previous step, which is then subjected to a coupling reaction with the next protected amino acid. The deprotection time of Fmoc deprotection is 10-60 min, preferably 15-25 min. The time of coupling reaction is 60-300 min, preferably 100-140 min.

The coupling reaction requires the addition of a condensation reagent, and the condensation reagent is selected from the group consisting of DIC (N,N-diisopropylcarbodiimide), N,N-dicyclohexylcarbodiimide, benzotriazole-1-yl-oxytripyrrolidinophosphonium hexafluorophosphate, 2-(7-aza-1H-benzotriazole-1-yl)-1,1,3,3-tetramethyluronium hexafluorophosphate, benzotriazole-N,N,N',N'-tetramethyluronium hexafluorophosphate and O-benzotriazole-N,N,N',N'-tetramethyluronium tetrafluoroborate; preferably N,N-diisopropylcarbodiimide. The molar amount of the condensation reagent is 1.2-6 times, preferably 2.5-3.5 times, of the total moles of amino groups in the amino resin.

The coupling reaction requires the addition of an activating agent, and the activating agent is selected from the group consisting of 1-hydroxybenzotriazole and N-hydroxy-7-azabenzotriazole, preferably 1-hydroxybenzotriazole. The amount of the activating agent is 1.2-6 times, preferably 2.5-3.5 times, of the total moles of amino groups in the amino resin.

As a preferred embodiment of the present disclosure, the reagent for removing Fmoc protection is a mixed solution of PTP/DMF (piperidine/N,N-dimethylformamide), and piperidine in the mixed solution is 10-30% (V). The amount of the de-Fmoc protecting agent is 5-15 mL per gram of amino resin, preferably 8-12 mL per gram of amino resin.

Preferably, the peptide resin is subjected to acid hydrolysis while removing the resin and the protecting group of side chain to obtain a crude product.

Further preferably, the acidolyzing agent used during acidolysis of the peptide resin is a mixed solvent of trifluoroacetic acid (TFA), 1,2-ethanedithiol (EDT) and water, and the volume percentage of each component in the mixed solvent is: TFA 80-95%, EDT 1-10%, and the balance is water.

More preferably, the volume percentage of each component in the mixed solvent is: TFA 89-91%, EDT 4-6%, and the balance is water. The optimal volume percentage of each component in the mixed solvent is: TFA 90%, EDT 5%, and the balance is water.

The amount of the acid hydrolyzing agent is 4-15 mL of acid hydrolyzing agent per gram of peptide resin; preferably, 7-10 mL of acid hydrolyzing agent per gram of peptide resin is required.

The time of the cleavage using the acid hydrolyzing agent is 1-6 hours at room temperature, preferably 3 to 4 hours.

Further, the crude product is purified by high performance liquid chromatography and freeze-dried to obtain a pure product.

1. Synthesis of Peptide Resin

The protected amino acids shown in the table below were sequentially coupled to Rink Amide BHHA resin as carrier resin by Fmoc deprotection and coupling reaction to prepare peptide resin. The protected amino acids used in this example are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc- Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhthr |
| 40 | Boc-His(Trt) |
| Side chain -1 | Fmoc-AEEA |
| Side chain -2 | Fmoc-AEEA |
| Side chain -3 | Fmoc-γGlu-OtBu |
| Side chain -4 | Mono-tert-butyl octadecanedioate |

Note
Dhthr: Dehydroxythreonine (1) Coupling a First Protected Amino Acid in the Main Chain 0.03 mol of the first protected amino acid and 0.03 mol of HOBt were dissolved in an appropriate amount of DMF. 0.03 mol of DIC was then slowly added to the DMIF solution of the protected amino acid under stirring, stirred and reacted at room temperature for 30 min to obtain an activated solution of the protected amino acid for later use.

0.01 mol of Rink amide MBHA resin (degree of substitution was about 0.4 mmol/g) was subjected to deprotection with 2000 PIP/DMF solution for 25 min, washed and filtered to obtain a Fmoc deprotection resin.

The activated solution of the first protected amino acid was added to the Fmoc deprotection resin for coupling reaction for 60-300 min, washed and filtered to obtain a resin containing the first protected amino acid.

(2) Coupling the 2nd to 40th Protected Amino Acids in the Main Chain

The above-mentioned corresponding 2nd to 40th protected amino acids were sequentially coupled by the same method as above for coupling the first protected amino acid in the main chain to obtain a resin containing 40 amino acids in the main chain.

(3) Coupling a First Protected Amino Acid in the Side Chain 0.03 mol of the side chain-1 protected amino acid and 0.03 mol of HOBt were dissolved in an appropriate amount of DMF. 0.03 mol of DIC was slowly added to the DMF solution of the protected amino acid under stirring, stirred and reacted at room temperature for 30 min to obtain the activated solution of the protected amino acid.

2.5 mmol of tetrakistriphenylphosphine palladium and 25 mmol of phenylsilane were dissolved in an appropriate amount of dichloromethane, subjected to deprotection for 4 hours, washed and filtered to obtain Alloc deprotection resin for later use.

The activated solution of the protected side chain-1 amino acid was added to the Alloc deprotection resin for coupling reaction for 60-300 min, washed and filtered to obtain a resin containing the protected side chain-1 amino acid.

(4) Coupling the 2nd to 4th Protected Amino Acids in the Side Chain

The 2nd to 4th protected amino acids corresponding to the side chain and monoprotected fatty acid were sequentially coupled by the same method as above for coupling the first protected amino acid in the main chain to obtain a peptide resin.

2. Preparation of Crude Product

To the above peptide resin, a cleavage agent with a volume ratio of TFA:water:EDT=95:5:5 (10 mL of cleavage agent/g of resin) was added, stirred evenly and reacted under stirring at room temperature for 3 h. The reaction mixture was filtered with a sand core funnel, the filtrate was collected, and the resin was washed three times with a small amount of TFA. The filtrates were combined, concentrated under reduced pressure, precipitated by adding anhydrous ether, washed with anhydrous ether three times, the liquid was removed and the precipitate was dried to obtain a crude product as an off-white powder.

3. Preparation of Pure Product

The above crude product was added with water and stirred. The pH of the solution was adjusted to 8.0 with aqueous ammonia until the crude product was completely dissolved. The solution was filtered with a 0.45 m mixed microporous filtration membrane for later purification.

The purification was performed by high-performance liquid chromatography. The chromatographic packing material for purification was 10 m reverse phase C18. The mobile phase system was 0.10% TFA/aqueous solution-0.1% TFA/acetonitrile solution. The flow rate of the 30 mm*250 mm chromatographic column was 20 mL/min. A gradient system was employed for elution, and the loading was cycled for purification. The solution with the crude product was loaded into the chromatographic column and then eluted with the mobile phase. The eluate of the main peak was collected and subjected to evaporation to remove acetonitrile to obtain a purified intermediate concentrate.

The purified intermediate concentrate was filtered with a 0.45 m filter membrane for later use. High-performance liquid chromatography was used for salt exchange. The mobile phase system was 1% acetic acid/aqueous solution-acetonitrile. The chromatographic packing material for purification was 10 m reverse phase C18. The flow rate of the 30 mm*250 mm chromatographic column was 20 mL/min (the corresponding flow rate can be adjusted according to the chromatographic column of different specifications). The method of gradient elution and cyclic sample loading was employed. The sample was loaded into the chromatographic column and then eluted with the mobile phase. The eluates were collected and subjected to spectrum analysis, and change in absorbance was observed. The eluate of the main peak during salt exchange was collected and detected for purity using analytical liquid phase. The eluate of the main peak during salt exchange was combined, concentrated under reduced pressure to obtain an aqueous acetic acid solution of pure product, which was then freeze-dried to obtain 7.7 g of pure product with a purity of 95.8%, a total yield of 15.2%, and a molecular weight of 5056.2 (100% M+H).

Example 2 Preparation of Compound 2

(SEQ ID NO: 3)

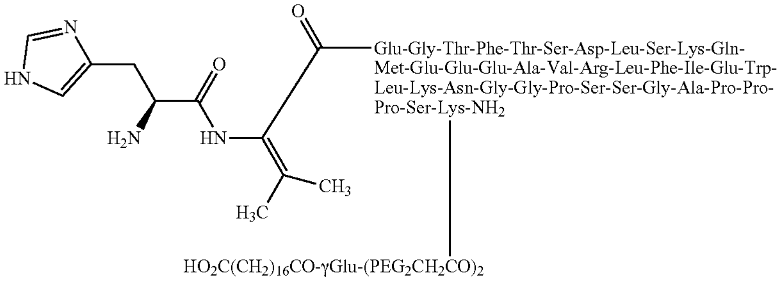

The preparation method was the same as in Example 1, and the protected amino acids used are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |

-continued

| Order of coupling AA, No. | Protected amino acid |
|---|---|
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc- Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhval |
| 40 | Boc-His(Trt) |
| Side chain-1 | Fmoc-AEEA |
| Side chain-2 | Fmoc-AEEA |
| Side chain-3 | Fmoc-γGlu-OtBu |
| Side chain-4 | Mono-tert-butyl octadecanedioate |

Note
Dhval: 2,3-Didehydrovaline 6.2 g of pure product was obtained with a purity of 95.8%, a total yield of 12.2% and a molecular weight of 5070.6 (100% M+H).

Example 3 Preparation of Compound 3

The preparation method was the same as in Example 1, and the protected amino acids used are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc- Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhthr |
| 40 | Boc-His(Trt) |
| Side chain-1 | Fmoc-$PEG_5CH_2COOH$ |
| Side chain-3 | Fmoc-γGlu-OtBu |
| Side chain-3 | Mono-tert-butyl octadecanedioate |

Note
Dhthr: Dehydroxythreonine (SEQ ID NO: 4)

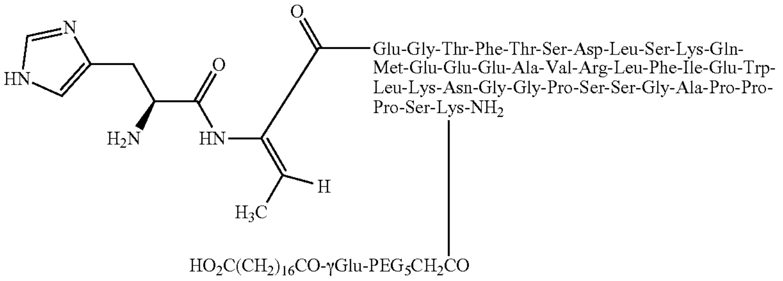

8.9 g of pure product was obtained with a purity of 98.5%, a total yield of 17.6% and a molecular weight of 5043.2 (100% M+H).

Example 4 Preparation of Compound 4

(SEQ ID NO: 5)

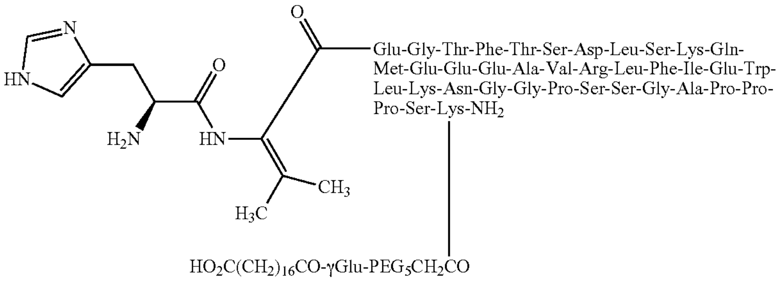

The preparation method was the same as in Example 1, and the protected amino acids used are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc-Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhval |
| 40 | Boc-His(Trt) |
| Side chain-1 | Fmoc-$PEG_5CH_2COOH$ |
| Side chain-2 | Fmoc-γGlu-OtBu |
| Side chain-3 | Mono-tert-butyl octadecanedioate |

Note
Dhval: 2,3-Didehydrovaline 5.2 g of pure product was obtained with a purity of 96.3%, a total yield of 10.3% and a molecular weight of 5057.6 (100% M+H).

Example 5 Preparation of Compound 5

(SEQ ID NO: 6)

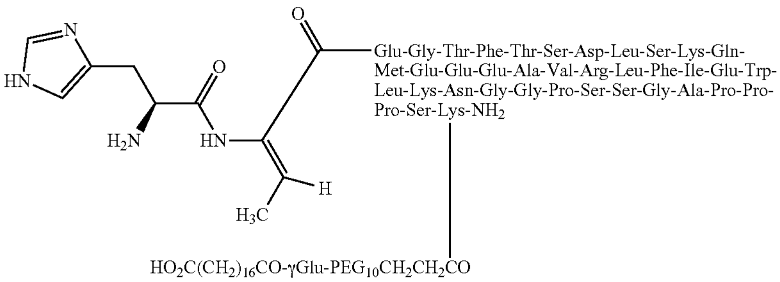

The preparation method was the same as in Example 1, and the protected amino acids used are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc-Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhthr |
| 40 | Boc-His(Trt) |
| Side chain-1 | Fmoc-$PEG_{10}CH_2COOH$ |
| Side chain-3 | Fmoc-γGlu-OtBu |
| Side chain-4 | Mono-tert-butyl octadecanedioate |

Note
Dhthr: Dehydroxythreonine 5.6 g of pure product was obtained with a purity of 97.6%, a total yield of 10.6% and a molecular weight of 5263.8 (100% M+H).

Example 6 Preparation of Compound 6

The preparation method was the same as in Example 1, and the protected amino acids used are as follows:

| Order of coupling AA, No. | Protected amino acid |
|---|---|
| 1 | Fmoc-Lys(Alloc) |
| 2 | Fmoc-Ser(tBu) |
| 3 | Fmoc-Pro |
| 4 | Fmoc-Pro |
| 5 | Fmoc-Pro |
| 6 | Fmoc-Ala |
| 7 | Fmoc-Gly |
| 8 | Fmoc-Ser(tBu) |
| 9 | Fmoc-Ser(tBu) |
| 10 | Fmoc-Pro |
| 11 | Fmoc-Gly |
| 12 | Fmoc-Gly |
| 13 | Fmoc-Asn(Trt) |
| 14 | Fmoc-Lys(Boc) |
| 15 | Fmoc-Leu |
| 16 | Fmoc-Trp(Boc) |
| 17 | Fmoc-Glu(OtBu) |
| 18 | Fmoc-Ile |
| 19 | Fmoc-Phe |
| 20 | Fmoc-Leu |
| 21 | Fmoc-Arg(pbf) |
| 22 | Fmoc-Val |
| 23 | Fmoc-Ala |
| 24 | Fmoc-Glu(OtBu) |
| 25 | Fmoc-Glu(OtBu) |
| 26 | Fmoc-Glu(OtBu) |
| 27 | Fmoc-Met |
| 28 | Fmoc-Gln(Trt) |
| 29 | Fmoc-Lys(Boc) |
| 30 | Fmoc-Ser(tBu) |
| 31 | Fmoc-Leu |
| 32 | Fm oc-Asp(OtBu) |
| 33 | Fmoc-Ser(tBu) |
| 34 | Fmoc-Thr(tBu) |
| 35 | Fmoc-Phe |
| 36 | Fmoc-Thr(tBu) |
| 37 | Fmoc-Gly |
| 38 | Fmoc-Glu(OtBu) |
| 39 | Fmoc-Dhval |
| 40 | Boc-His(Trt) |
| Side chain-1 | Fmoc-$PEG_{10}CH_2COOH$ |
| Side chain-2 | Fmoc-γGlu-OtBu |
| Side chain-3 | Mono-tert-butyl octadecanedioate |

Note
Dhval: 2,3-Didehydrovaline 4.5 g of pure product was obtained with a purity of 97.1%, a total yield of 8.5% and a molecular weight of 5277.6 (100% M+H).

(SEQ ID NO: 7)

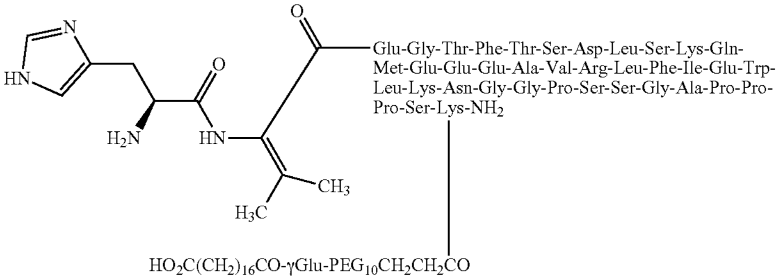

Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Lys-$NH_2$ $HO_2C(CH_2)_{16}CO$-γGlu-$PEG_{10}CH_2CH_2CO$

Example 7 Activity Detection

1. Method

GLP-1R, mainly present on the surface of islet R cells, is a G protein-coupled receptor (GPCR). Under the stimulation of specific agonist, GLP-1R can activate the intracellular adenylate cyclase pathway, increase the level of cAMP, and finally lead to the production and release of insulin. By stimulating the stable cell line expressing GLP-1R with the agonist to be tested, the intracellular cAMP level will rapidly increase, and the relative light units (RLUs) after stimulating the cells at each dose are determined by chemiluminescence method to calculate the $EC_{50}$ of the agonist. This method for activity detection is commonly used for GLP-1 receptor agonist activity analysis at home and abroad.

CHO-K1 stable cell line expressing GLP-1R was used in the experiment. The cells were stimulated with different concentrations of agonist, the relative light units after stimulating the cells at each dose were measured, and the biological activity of the agonist was obtained.

2. Results

The results are shown in the table below.

| Compound No. | Biological Activity (%) |
|---|---|
| Compound 1 | 52.64 |
| Compound 2 | 18.14 |
| Compound 3 | 82.92 |
| Compound 4 | 20.25 |
| Compound 5 | 46.48 |
| Compound 6 | 14.51 |

Example 8 Preliminary Determination of Pharmacokinetic Properties

Each compound was tested in two administration groups. SD rats were used, 4 males and 4 females in each group, 8 rats in total.

Tail vein intravenous injection group: The dose was 1 mg/kg. Blood samples were collected from the orbital vein of the rats before administration (0 h) and 30 min, 1 h, 2 h, 4 h, 8 h, 24 h, 48 h, 96 h, and 144 h after administration. Plasma samples were collected after centrifugation.

Subcutaneous administration group: The dose was 1 mg/kg. Blood samples were collected from the orbital vein of the rats before administration (0 h) and 1 h, 2 h, 3 h, 4 h, 8 h, 24 h, 48 h, 96 h, and 144 h after administration. Plasma samples were collected after centrifugation.

The concentrations of the corresponding compounds in the plasma samples from SD rats were determined by LC/MS. After intravenous and subcutaneous administration, the half-life of compounds in subcutaneously (SC) administered SD rats is shown in the following table:

| Compound | $t_{1/2}$ (h) |
|---|---|
| Compound 1 | 8.9 |
| Compound 2 | 8.4 |
| Compound 3 | 8.7 |
| Compound 4 | 8.9 |
| Compound 5 | 10.5 |
| Compound 6 | 10.1 |

The invention claimed is:

1. An exenatide analog having structure I:

AA1-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-AA2(R)-AA3 (SEQ ID NO: 1)

wherein AA1 of structure I is:

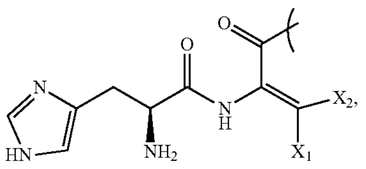

$X_1$ is $CH_3$ and $X_2$ is H;

AA2 of structure I is Lys;

AA3 of structure I is $NH_2$ or OH; and

R of structure I is $HO_2C(CH_2)_{n1}CO—(\gamma Glu)_{n2}\text{-}(PEG_{n3}(CH_2)_{n4}CO)_{n5}—$, n1 is an integer from 10 to 20, n2 is an integer from 1 to 5, n3 is an integer from 1 to 30, n4 is an integer from 1 to 5, and n5 is an integer from 1 to 5.

2. The exenatide analog according to claim 1, which is a pharmaceutically acceptable salt thereof, a solvate thereof, or any mixture thereof.

3. A pharmaceutical composition comprising the exenatide analog according to claim 1.

4. A method for treating a disease comprising administering the exenatide analog according to claim 1 to a subject in need thereof, wherein the disease is selected from the group consisting of type II diabetes, impaired glucose tolerance, type I diabetes and obesity.

5. The method according to claim 4, wherein the disease is type II diabetes with delayed efficacy.

6. A method for reducing food intake, reducing β-cell apoptosis, increasing islet β-cell function, increasing β cells and/or restoring β-cell sensitivity to glucose, comprising administering the exenatide analog according to claim 1 to a subject in need thereof.

7. A method for regulating blood glucose in vivo comprising administering the exenatide analog according to claim 1 to a subject in need thereof.

8. A method for preventing the exacerbation of type II diabetes comprising administering the exenatide analog according to claim 1 to a subject in need thereof.

* * * * *

SEQUENCE LISTING

```
<160> NUMBER OF SEQ ID NOS: 7

<210> SEQ ID NO 1
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is an artificial amino acid defined by X1
      and X2. X1 and X2 are each independently H, CH3, CH(CH3)2,
      C(CH3)3, CH(CH2CH3)2, C(CH2CH3)3, CH(CH2CH2CH3)2, C(CH2CH2CH3)3,
      CH(CH(CH3))2, C(CH(CH3))3, CH2CH3, CH2CH(CH3)2, or CH2C(CH3)3.
<220> FEATURE:
<221> NAME/KEY: VARIANT
<222> LOCATION: (2)..(2)
<223> OTHER INFORMATION: Xaa is an artificial amino acid defined by X1
      and X2. X1 and X2 are each independently CH2CH(CH2CH3)2,
      CH2C(CH2CH3)3, CH2CH(CH2CH2CH3)2, CH2C(CH2CH2CH3)3,
      CH2CH(CH(CH3))2, or CH2C(CH(CH3))3.
<220> FEATURE:
<221> NAME/KEY: VARIANT
<222> LOCATION: (40)..(40)
<223> OTHER INFORMATION: This amino acid has a free group of -NH2 or
      -OH.
<220> FEATURE:
<221> NAME/KEY: VARIANT
<222> LOCATION: (40)..(40)
<223> OTHER INFORMATION: Xaa is Lys, Dah, Orn, Dab or Dap.
<220> FEATURE:
<221> NAME/KEY: VARIANT
```

-continued

<222> LOCATION: (40)..(40)
<223> OTHER INFORMATION: This amino acid is modified with HO2C(CH2)n1CO-(gamma Glu)n2-(PEGn3(CH2)n4CO)n5-, n1 is an integer from 10 to 20, n2 is an integer from 1 to 5, n3 is an integer from 1 to 30, n4 is an integer from 1 to 5, and n5 is an integer from 1 to 5.

<400> SEQUENCE: 1

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40
```

<210> SEQ ID NO 2
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhThr.
<220> FEATURE:
<221> NAME/KEY: VARIANT
<222> LOCATION: (40)..(40)
<223> OTHER INFORMATION: Modified with HO2C(CH2)16CO-gammaGlu-(PEG2CH2CO)2
<220> FEATURE:
<221> NAME/KEY: VARIANT
<222> LOCATION: (40)..(40)
<223> OTHER INFORMATION: This animo acid has a free group of -NH2.

<400> SEQUENCE: 2

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```

<210> SEQ ID NO 3
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhVal.
<220> FEATURE:
<221> NAME/KEY: VARIANT
<222> LOCATION: (40)..(40)
<223> OTHER INFORMATION: Modified with HO2C(CH2)16CO-gammaGlu-(PEG2CH2CO)2
<220> FEATURE:
<221> NAME/KEY: VARIANT
<222> LOCATION: (40)..(40)
<223> OTHER INFORMATION: This amino acid has a free group of -NH2.

<400> SEQUENCE: 3

```
His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Pro Ser Lys
35 40

<210> SEQ ID NO 4
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhThr.
<220> FEATURE:
<221> NAME/KEY: VARIANT
<222> LOCATION: (40)..(40)
<223> OTHER INFORMATION: Modified with HO2C(CH2)16CO-gammaGlu-PEG5CH2CO
<220> FEATURE:
<221> NAME/KEY: VARIANT
<222> LOCATION: (40)..(40)
<223> OTHER INFORMATION: This amino acid has a free group of -NH2.

<400> SEQUENCE: 4

His Xaa Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Pro Ser
20 25 30

Ser Gly Ala Pro Pro Pro Ser Lys
35 40

<210> SEQ ID NO 5
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhVal.
<220> FEATURE:
<221> NAME/KEY: VARIANT
<222> LOCATION: (40)..(40)
<223> OTHER INFORMATION: Modified with HO2C(CH2)16CO-gammaGlu-PEG5CH2CO
<220> FEATURE:
<221> NAME/KEY: VARIANT
<222> LOCATION: (40)..(40)
<223> OTHER INFORMATION: This amino acid has a free group of -NH2.

<400> SEQUENCE: 5

His Xaa Glu Gly Thr Phe Thr Ser Asp Leu Ser Lys Gln Met Glu Glu
1 5 10 15

Glu Ala Val Arg Leu Phe Ile Glu Trp Leu Lys Asn Gly Gly Pro Ser
20 25 30

Ser Gly Ala Pro Pro Pro Ser Lys
35 40

<210> SEQ ID NO 6
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhThr.
<220> FEATURE:
<221> NAME/KEY: VARIANT
<222> LOCATION: (40)..(40)

-continued

```
<223> OTHER INFORMATION: Modified with HO2C(CH2)16CO-gammaGlu-
      PEG10CH2CH2CO
<220> FEATURE:
<221> NAME/KEY: VARIANT
<222> LOCATION: (40)..(40)
<223> OTHER INFORMATION: This amino acid has a free group of -NH2.

<400> SEQUENCE: 6

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40


<210> SEQ ID NO 7
<211> LENGTH: 40
<212> TYPE: PRT
<213> ORGANISM: Artificial Sequence
<220> FEATURE:
<223> OTHER INFORMATION: glucagon-like peptide-1 (GLP-1) analog
<220> FEATURE:
<221> NAME/KEY: VARIANT
<222> LOCATION: (2)..(2)
<223> OTHER INFORMATION: Xaa is DhVal.
<220> FEATURE:
<221> NAME/KEY: VARIANT
<222> LOCATION: (40)..(40)
<223> OTHER INFORMATION: Modified with HO2C(CH2)16CO-gammaGlu-
      PEG10CH2CH2CO
<220> FEATURE:
<221> NAME/KEY: VARIANT
<222> LOCATION: (40)..(40)
<223> OTHER INFORMATION: This amino acid has a free group of -NH2.

<400> SEQUENCE: 7

His Xaa Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```